United States Patent
Nolan et al.

(10) Patent No.: US 9,480,849 B2
(45) Date of Patent: Nov. 1, 2016

(54) METHOD OF OVERMOULDING TOP MOUNTED SEAL PLUG CAVITIES

(71) Applicant: Cardiac Pacemakers, Inc., St. Paul, MN (US)

(72) Inventors: Daragh Nolan, Via Youghal (IE); James M. English, Cahir (IE); Richard Percy, Leamlara (IE); Sean Walsh, Clare (IE); John O'Rourke, Tip (IE)

(73) Assignee: Cardiac Pacemakers, Inc., St. Paul, MN (US)

( * ) Notice: Subject to any disclaimer, the term of this patent is extended or adjusted under 35 U.S.C. 154(b) by 12 days.

(21) Appl. No.: 14/327,876

(22) Filed: Jul. 10, 2014

(65) Prior Publication Data

US 2015/0018922 A1    Jan. 15, 2015

Related U.S. Application Data

(60) Provisional application No. 61/845,570, filed on Jul. 12, 2013.

(51) Int. Cl.

| | | |
|---|---|---|
| *A61N 1/375* | (2006.01) | |
| *A61N 1/362* | (2006.01) | |
| *A61N 1/39* | (2006.01) | |
| *B29C 45/14* | (2006.01) | |
| *B29L 31/00* | (2006.01) | |
| *B29K 659/00* | (2006.01) | |
| *B29C 45/26* | (2006.01) | |

(52) U.S. Cl.
CPC ............. *A61N 1/375* (2013.01); *A61N 1/3968* (2013.01); *B29C 45/14754* (2013.01); *A61N 1/362* (2013.01); *B29C 45/2628* (2013.01); *B29C 2045/1477* (2013.01); *B29K 2659/00* (2013.01); *B29K 2883/005* (2013.01); *B29L 2031/753* (2013.01)

(58) Field of Classification Search
CPC ..................... A61N 1/375; A61N 1/3752
See application file for complete search history.

(56) References Cited

U.S. PATENT DOCUMENTS

| | | |
|---|---|---|
| 3,822,707 A | 7/1974 | Adducci |
| 3,908,668 A | 9/1975 | Bolduc |
| 4,072,154 A | 2/1978 | Anderson et al. |
| 4,105,037 A | 8/1978 | Richter et al. |
| 4,141,752 A | 2/1979 | Shipko |
| 4,180,078 A | 12/1979 | Anderson |
| 4,461,194 A | 7/1984 | Moore |
| 4,479,489 A | 10/1984 | Tucci |
| 5,012,807 A | 5/1991 | Stutz, Jr. |
| 5,086,773 A | 2/1992 | Ware |
| 6,817,905 B2 | 11/2004 | Zart et al. |
| 7,155,283 B2 | 12/2006 | Ries et al. |
| 7,955,543 B2 | 6/2011 | Deininger et al. |
| 8,103,348 B1 | 1/2012 | Coffed et al. |
| 8,315,700 B2 | 11/2012 | Citron et al. |
| 2002/0107555 A1 | 8/2002 | Rusin et al. |
| 2004/0122481 A1 | 6/2004 | Tidemand et al. |
| 2006/0015150 A1 | 1/2006 | Rusin et al. |
| 2011/0160808 A1 | 6/2011 | Lyden et al. |
| 2012/0090161 A1 | 4/2012 | Biggs, Jr. et al. |

*Primary Examiner* — Brian T Gedeon
(74) *Attorney, Agent, or Firm* — Schwegman Lundberg & Woessner, P.A.

(57) ABSTRACT

A method includes providing a mold defining a mold cavity for receiving material to be molded into a molded part, positioning an insert at least partially in the mold such that a portion of the insert defines a portion of the mold cavity, and injecting the material into the mold cavity to substantially fill the mold cavity to form the molded part. The molded par can then be removed from the mold and the insert can be removed from the molded part. The mold can include silicone and the insert can include polyoxymethylene.

20 Claims, 8 Drawing Sheets

METHOD OF OVERMOULDING TOP MOUNTED SEAL PLUG CAVITIES

CROSS-REFERENCE TO RELATED APPLICATION

This application claims priority to Provisional Application No. 61/845,570, filed Jul. 12, 2013, which is herein incorporated by reference in its entirety.

TECHNICAL FIELD

The present invention relates to implantable medical devices. More specifically, the invention relates to molded headers for implantable medical devices.

BACKGROUND

Various physiological functions can be managed and/or monitored using medical devices. Many such medical devices are implantable in a human body, such as implantable cardioverter-defibrillators (ICDs) or pacemakers. Such devices typically include a housing enclosing the device and may or may not include one or more medical electrical leads that can transmit electrical signals to and/or from a sensor, electrode, or other electrical component at a distal end of the medical electrical lead. For example, such devices have been used in association with cardiac rhythm management, which can include cardiac pacing, cardiac defibrillation, and/or cardiac therapy, among other procedures.

In some such devices, the housing can isolate internal components from conductive bodily fluids after implant. Various designs for such housings are known in the art, some of which include headers for connecting the medical electrical leads to the device. There exists a need for alternative designs for headers and associated components for such implantable medical devices.

SUMMARY

Disclosed herein are various embodiments of medical devices and methods of molding a header of a medical device.

In Example 1, a method includes providing a mold defining a mold cavity for receiving material to be molded into a molded part and positioning an insert at least partially in the mold such that a portion of the insert defines a portion of the mold cavity. The mold includes silicone and the insert includes polyoxymethylene. The material can be injected into the mold cavity to substantially fill the mold cavity to form the molded part. The molded part can be removed from the mold the insert can be removed from the molded part.

In Example 2, the method according to Example 1, wherein the insert is entirely contained in the mold and defines a shape of a portion of an outer surface of the molded part.

In Example 3, the method according to any of Examples 1-2, wherein the insert consists or consists essentially of polyoxymethylene homopolymer.

In Example 4, the method according to any of Examples 1-3, wherein the material comprises epoxy.

In Example 5, the method according to any of Examples 1-4, and further including positioning a pin in the mold cavity adjacent the insert prior to injecting the material into the mold cavity, wherein the pin comprises polyoxymethylene, and wherein the pin defines a shape of a hole of the molded part; and removing the pin from the molded part after the molded part is formed.

In Example 6, the method according to any of Examples 1-5, wherein the molded part comprises a header for an implantable medical device.

In Example 7, the method according to any of Examples 1-6, wherein the insert defines a shape of a ridge on a surface of the molded part extending between holes defined by the molded part.

In Example 8, the method according to Example 7, wherein the ridge has a thickness of about 0.9 millimeters or less.

In Example 9, a method includes providing a mold defining an internal cavity and positioning an insert in the internal cavity so that the insert is entirely contained in the mold. The internal cavity includes a mold cavity for receiving material to be molded into a header for an implantable medical device and including an insert cavity adjacent the mold cavity. At least a portion of the insert is positioned in the insert cavity. A surface of the insert defines a portion of a top of the mold cavity. The material can be injected into the mold cavity to substantially fill the mold cavity to form the header. The header can be removed from the mold and the insert can be removed from the header.

In Example 10, the method according to Example 9, wherein the insert comprises a polyoxymethylene homopolymer.

In Example 11, the method according to any of Examples 9-10, wherein the mold comprises silicone.

In Example 12, the method according to any of Examples 9-11, wherein the material comprises epoxy.

In Example 13, the method according to any of Examples 9-12, and further including positioning a pin in the mold cavity adjacent the insert prior to injecting the material into the mold cavity and removing the pin from the header after the molded part is formed. The pin can define a shape of a set screw hole of the header.

In Example 14, the method according to Example 13, and further including inserting a seal plug into the set screw hole, wherein the seal plug has a deformable slit extending through a top of the seal plug through which a tool can be inserted and that is substantially closed to seal and limit fluid flow through the seal plug when the tool is removed.

In Example 15, the method according to any of Examples 13-14, wherein the pin comprises a polyoxymethylene homopolymer.

In Example 16, the method according to any of Examples 13-15, and further including positioning a core in the mold cavity adjacent the insert prior to injecting the material into the mold cavity, wherein the pin extends from the core to the insert when the material is injected into the mold cavity.

In Example 17, the method according to any of Examples 9-16, and further including positioning a device housing at least partially in the mold and molding the header so as to attach the header to the device housing during molding.

In Example 18, the method according to any of Examples 9-17, wherein the insert defines a shape of a portion of an outer surface of the header at a top of the header.

In Example 19, an implantable pulse generator includes a device housing and a header molded to the device housing. The header is formed of an epoxy header material. The header a top surface opposite the device housing and defines a plurality of set screw holes extending into the header on the top surface. The header includes a ridge on the top surface between the set screw holes. A plurality of seal plugs can be positioned in the set screw holes so as to fluidically seal the set screw holes. The seal plug has a deformable slit extending through a top of the seal plug through which a tool can be inserted and that is substantially closed to seal and limit fluid flow through the seal plug when the tool is removed.

In Example 20, the implantable pulse generator according to Example 19, wherein the ridge has a thickness of about 0.9 millimeters or less.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
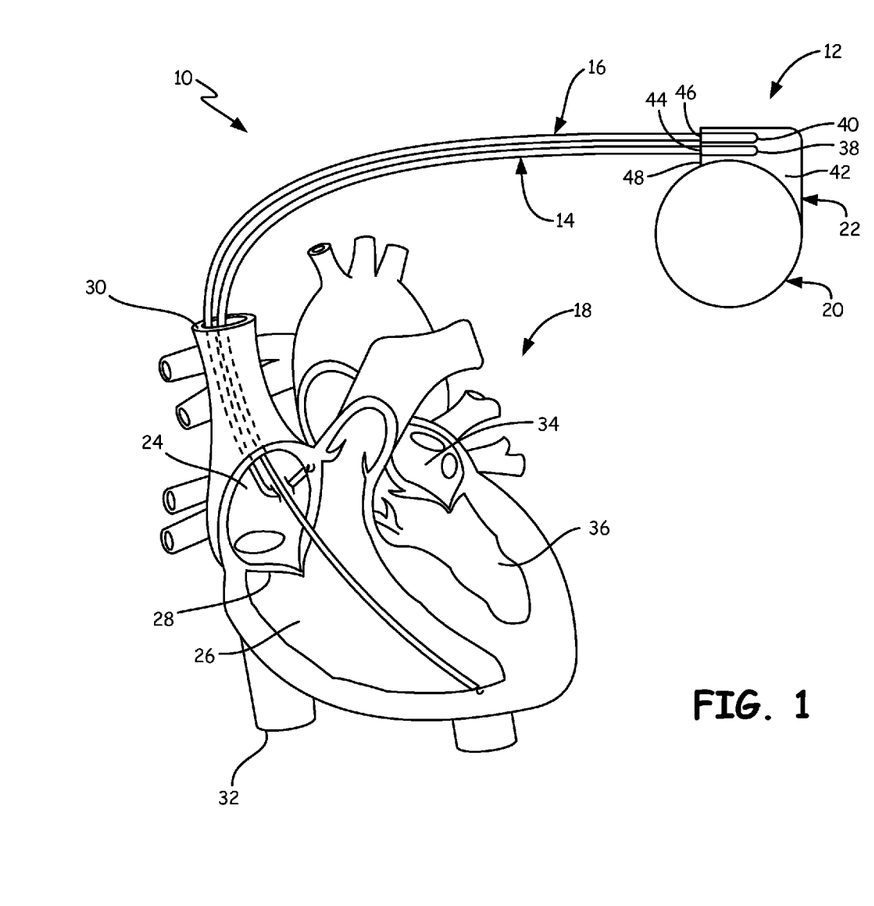
FIG. 1 is a schematic view of a cardiac rhythm management (CRM) system according to one embodiment of the present invention.

FIG. 1 is a schematic view of a cardiac rhythm management (CRM) system 10 according to one embodiment. As shown in FIG. 1, the CRM system 10 includes a pulse generator 12 coupled to a plurality of leads 14 and 16 deployed in a patient's heart 18. The pulse generator 12 includes a housing 20 and a header 22 mounted on the housing 20. As further shown in FIG. 1, the heart 18 includes a right atrium 24 and a right ventricle 26 separated by a tricuspid valve 28. During normal operation of the heart 18, deoxygenated blood is fed into the right atrium 24 through the superior vena cava 30 and the inferior vena cava 32. As further shown, the heart 18 includes a left atrium 34, which receives oxygenated blood from the lungs, and a left ventricle 36, which pumps the oxygenated blood to the body.

The leads 14 and 16 are medical electrical leads that operate to convey electrical signals and stimuli between the heart 18 and the pulse generator 12. The header 22 of the pulse generator 12 is an output terminal header with cores 38 and 40 substantially encapsulated in a header body 42. The cores 38 and 40 are output terminal cores for receiving proximal ends of the leads 14 and 16, respectively. The leads 14 and 16 are attached to the header 22 by inserting the proximal ends of the leads 14 and 16 into receptacles 44 and 46 positioned on a front surface 48 of the header 22. In the illustrated embodiment, a distal end of the lead 14 is implanted in the right ventricle 26, and a distal end of the lead 16 is implanted in the right atrium 24. In other embodiments, the CRM system 10 may include additional leads, e.g., a lead extending into a coronary vein for stimulating the left ventricle in a bi-ventricular pacing or cardiac resynchronization therapy (CRT) system. As shown, the leads 14 and 16 enter the superior vena cava 30, and are implanted in the right ventricle 26 and right atrium 24, respectively.

The pulse generator 12 can be implanted subcutaneously within an implantation location or pocket in the patient's chest or abdomen. The pulse generator 12 can be an implantable medical device known in the art, or later developed, for delivering an electrical therapeutic stimulus to the patient. In various embodiments, the pulse generator 12 can be a neurostimulation device, a pacemaker, a CRT device, an implantable cardiac defibrillator, and/or can include both pacing, CRT and/or defibrillation capabilities (e.g., a CRT-D device).

In some embodiments the CRM system 10 can be configured to stimulate cardiac tissue and/or sense certain physiological attributes of the heart. However, in discussing embodiments of the present disclosure, reference is made primarily to stimulating body tissues. Those of ordinary skill in the art will recognize that some or all of the configurations can also be used to receive electrical signals from the body.

Figure 2:
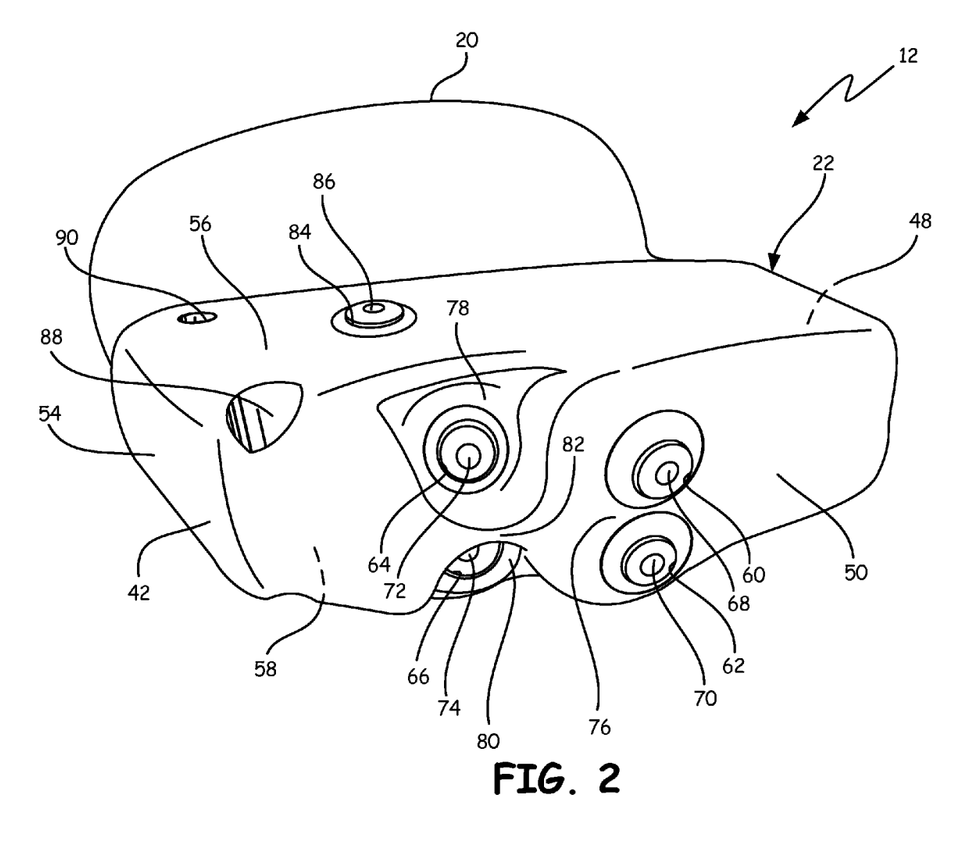
FIG. 2 is a perspective view of one embodiment of a pulse generator, having a header and a housing, for use in the CRM system of FIG. 1.

FIG. 2 is a perspective view of one embodiment of the pulse generator 12, including the header 22 and the housing 20. The header 22 has a top surface 50, a bottom surface 52, a back surface 54, and two sides surfaces 56 and 58, in addition to the front surface 48. The top surface 50, the back surface 54, and the side surface 56 are all visible in FIG. 2, while the front surface 48, the bottom surface 52, and the side surface 58 are at least partially obscured.

The bottom surface 52 of the header 22 is attached to the housing 20. The bottom surface 52 can be attached to the housing 20 by molding the header 22 to the housing 20 as further described below. The top surface 50 is positioned opposite of the bottom surface 52, and consequently is positioned opposite of the housing 20.

The front surface 48 extends from the top surface 50 to the bottom surface 52 and can include a plurality of terminal holes (such as receptacles 44 and 46 shown in FIG. 1) for receiving and connecting to lead terminals. The back surface 54 is positioned opposite the front surface 48, and also extends from the top surface 50 to the bottom surface 52.

The side surface 56 extends between the front surface 48 and the back surface 54, and also extends between the top surface 50 and the bottom surface 52. The side surface 58 is positioned opposite the side surface 56, and also extends between the front surface 48 and the back surface 54, and between the top surface 50 and the bottom surface 52.

The header 22 defines a plurality of holes 60, 62, 64, and 66 at the top surface 50 of the header 22. The holes 60, 62, 64, and 66 are set screw holes that allow access to set screws (not shown) that can be tightened to fasten the lead terminals of leads (such as the leads 14 and 16 shown in FIG. 1) into cores (such as the cores 38 and 40 shown in FIG. 1). The plugs 68, 70, 72, and 74 are seal plugs that are inserted into and seal the holes 60, 62, 64, and 66, respectively. The plugs 68, 70, 72, and 74 have deformable slits (not shown) extending through the plugs 68, 70, 72, and 74 to allow a tool (not shown) to be inserted through the slits to rotate the set screws positioned under the plugs 68, 70, 72, and 74. When the tool is removed, the slits can resiliently return to their original, sealed configuration.

The top surface 50 has a raised portion 76, sunken portions 78 and 80, and a ridge 82 extending between the sunken portions 78 and 80. The sunken portions 78 and 80 are sunken toward the bottom surface 52, and the raised portion 76 and ridge 82 are raised away from the bottom surface 52. The raised portion 76 is positioned on the top surface 50 between the front surface 48 and the sunken portions 78 and 80. The sunken portions 78 and 80 are positioned on the top surface 50 between the back surface 54 and the raised portion 76. The holes 60 and 62 extend through the top surface 50 at the raised portion 76. The hole 64 extends through the top surface 50 at the sunken portion 78. The hole 66 extends through the top surface 50 at the sunken portion 80. The ridge 82 can be formed with a relatively small thickness. For example, in one embodiment, the ridge 82 can have a thickness of about 0.9 millimeters or less.

A hole 84 is another set screw hole, extending into header 22 and is positioned on the side surface 56. A plug 86 is another seal plug that seals the hole 84. The hole 84 is aligned substantially orthogonal to the holes 60, 62, 64, and 66, as well as orthogonal to the receptacles 44 and 46. The holes 60, 62, 64, and 66 are substantially parallel to one another, but are substantially orthogonal to the hole 84 and the receptacles 44 and 46. Though not shown, a sixth set screw hole and sixth seal plug can be positioned on the side surface 58. The six set screw holes can correspond to six receptacles (such as the receptacles 44 and 46 shown in FIG. 1) on the front surface 48. In alternative embodiments, the header 44 can have fewer or more than six seal plugs, set screw holes, and receptacles, which can be positioned and oriented differently than as illustrated.

Two suture holes 88 and 90 extend through the header 22 from the side surface 56 to the side surface 58. The suture holes 88 and 90 can be used to hold the pulse generator 12 in place when implanted in a human body of a medical patient. Sutures (not shown) or other fasteners can extend through the suture holes 88 and 90 to attach the header 22 to tissue of the medical patient.

The header 22 can be formed by injection molding as described below, resulting in the header body 42 (including the front surface 48, the top surface 50, the bottom surface 52, the back surface 54, and the sides surfaces 56 and 58) being formed in the shape substantially as illustrated.

Figure 3:
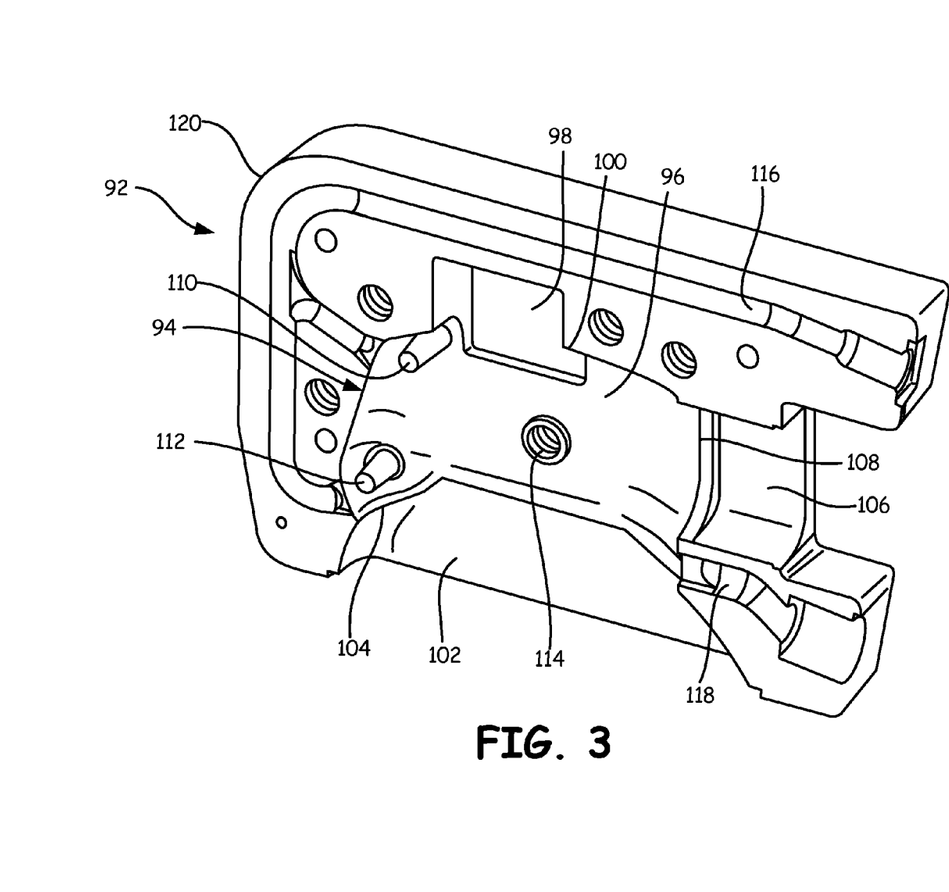
FIG. 3 is a perspective view of a mold for use in forming the header of the pulse generator.

FIG. 3 is a perspective view of a mold 92 for forming the shape of the header 22 (shown in FIGS. 1 and 2) of the pulse generator 12 (shown in FIGS. 1 and 2). The mold 92 defines an internal cavity 94, which includes a mold cavity 96 and an insert cavity 98. The insert cavity 98 is adjacent the mold cavity 96 at a top 100 of the mold cavity 96. The insert cavity 98 is fluidically connected to the mold cavity 96. A housing cavity 102 is adjacent the mold cavity 96 at a bottom 104 of the mold cavity 96. The housing cavity 102 is sized and shaped for the housing 20 (shown in FIGS. 1 and 2) to be positioned at least partially in the mold 92. A pin assembly cavity 106 is also adjacent the mold cavity 96 at a front 108 of the mold cavity 96. The pin assembly cavity 106 is sized and shaped to hold a pin assembly (shown in FIG. 4).

The mold 92 has two shafts 110 and 112 that extend into the mold cavity 96 for forming the shape of the suture holes 88 and 90. The mold 92 defines a hole 114 extending through the mold 104 for allowing a molding pin (not shown) to be inserted into the mold cavity 96 for forming the shape of the hole 84 (shown in FIG. 2) in the header 22.

Runners 116 and 118 extend through the mold 92 to the mold cavity 96, allowing material to be injected into the mold cavity 96 from a supply (not shown) of molding material.

Although only a single mold die 120 of the mold 92 is shown, it should be understood that the mold die 120 can be combined with one or more corresponding mold dies to substantially enclose the internal cavity 94. For example, the mold die 120 can be used in conjunction with a second mold die that is a mirror image of the mold die 120. The mold 92, including the mold die 120, can be formed of a silicone material. In one embodiment, the mold 92 can be made from a two part liquid injection silicone. In another embodiment, the mold 92 can be made from a compression molded silicone. In another embodiment, the mold 92 can be made from a room temperature vulcanizing silicone. In one embodiment, the mold 92 can consist or consist essentially of silicone. In alternative embodiments, the mold 92 can include other materials in addition to or instead of silicone.

Figure 4:
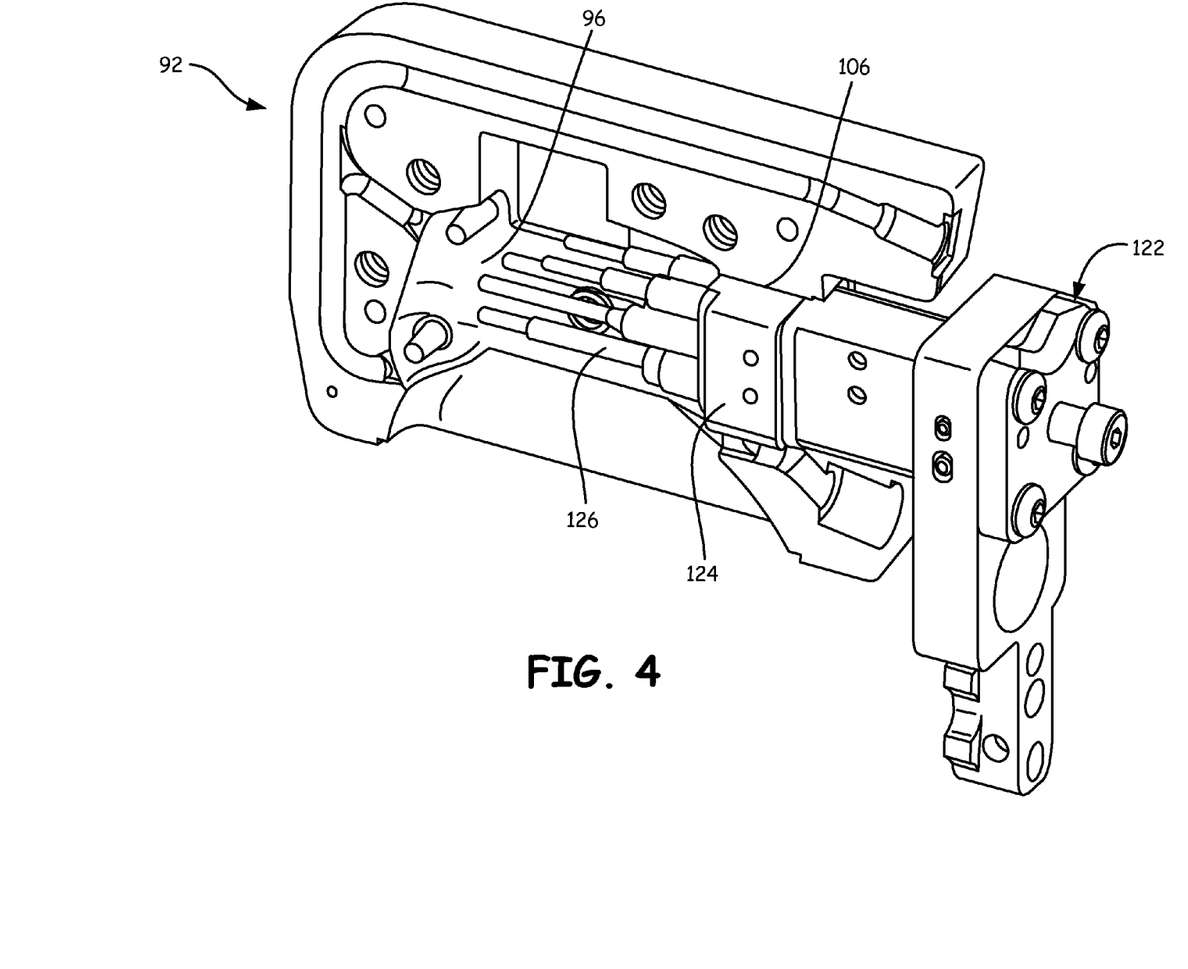
FIG. 4 is a perspective view of the mold with a pin assembly positioned therein.

FIG. 4 is a perspective view of the mold 92 with a pin assembly 122 positioned in the pin assembly cavity 106. The pin assembly 122 includes a base 124 and a plurality of pins 126 extending from the base 124 into the mold cavity 96. The pins 126 form the shape of the receptacles (such as receptacles 44 and 46 shown in FIG. 1) of the header 22 (shown in FIGS. 1 and 2). The pins 126 are removable from the header 22 once the header 22 has been formed.

Figure 5:
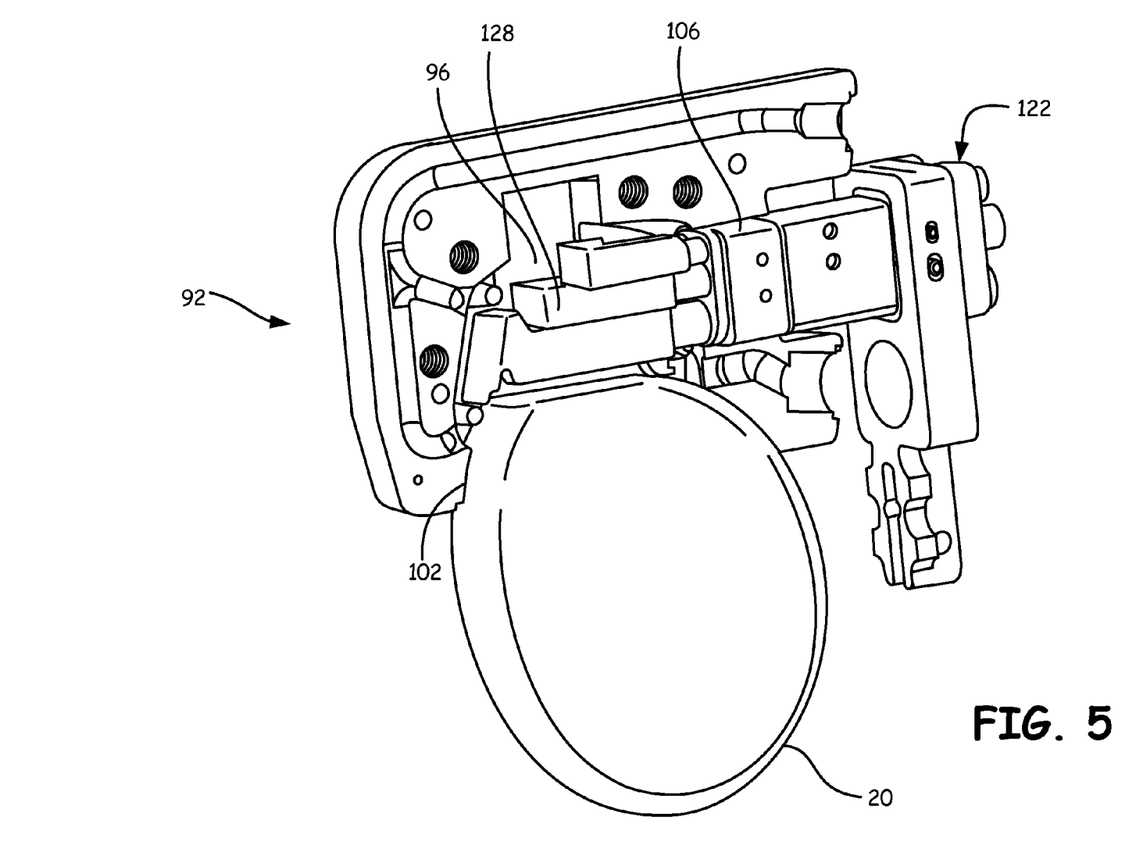
FIG. 5 is a perspective view of the mold with the pin assembly, a core, and the housing positioned therein.

FIG. 5 is a perspective view of the mold 92, with the pin assembly 122 positioned in the pin assembly cavity 106, the housing 20 positioned in the housing cavity 102, and a core 128 positioned in the mold cavity 96. The core 128 can be electrically connected to pulse generator circuitry (not shown) in the housing via a plurality of leads (not shown). The core 128 can include a plurality of electrically conductive tip blocks, set screws, and lead bore cavities (not shown) that electrically connect the pulse generator 12 (shown in FIGS. 1 and 2) to the leads 14 and 16 (shown in FIG. 1). The core 128 is mounted on the pin assembly 122 so as to be spaced from the mold 92, allowing material to flow around the core 128 so as to form the header body 42 (shown in FIGS. 1 and 2) of the header 22 and encapsulate the core 128. In alternative embodiments, the core 128 can be omitted and replaced by an alternative electrical conductor assembly.

Figure 6:
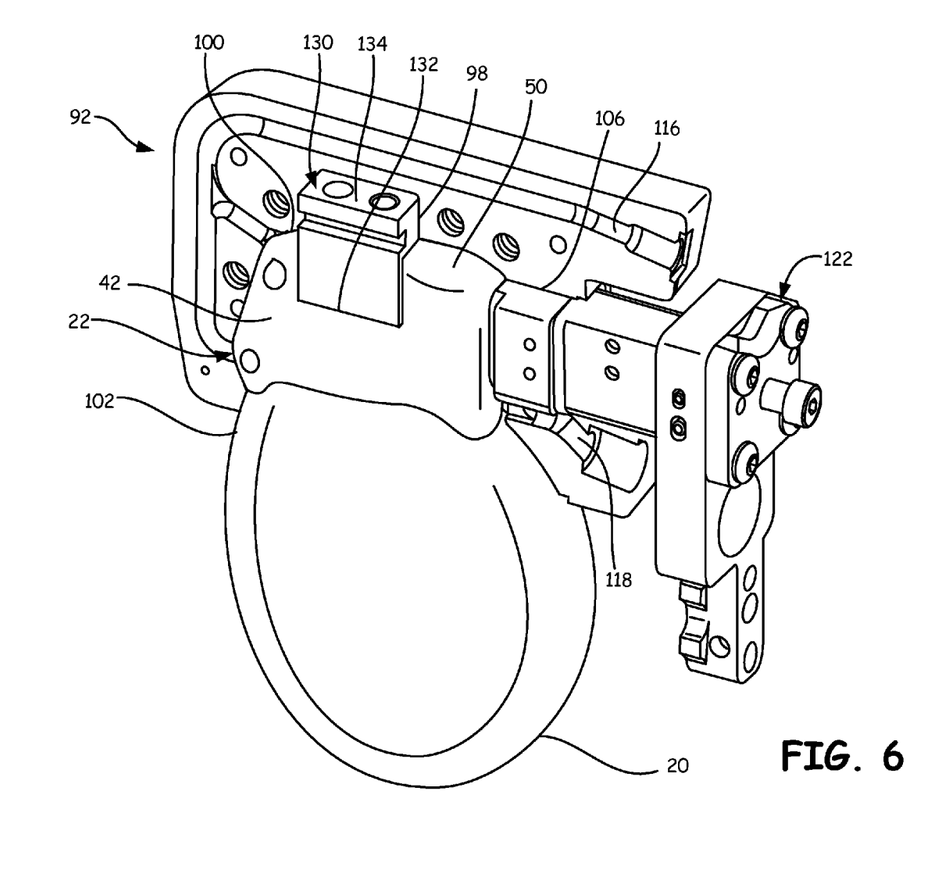
FIG. 6 is a perspective view of the mold with the pin assembly, the housing, the header, and an insert positioned therein.

FIG. 6 is a perspective view of the mold 92, with the pin assembly 122 positioned in the pin assembly cavity 106, the housing 20 positioned in the housing cavity 102, an insert 130 positioned in the insert cavity 98, and the header body 42 positioned and formed in the mold cavity 96. The insert 130 is positioned at least partially in the mold 92. In the illustrated embodiment, the insert 130 is positioned in the internal cavity 94 of the mold 92 so that the insert 130 is entirely contained in the mold 92. A bottom portion 132 of the insert 130 defines a top 100 of the mold cavity 96 for forming part of the top surface 50 of the header body 42. A top portion 134 of the insert 130 is positioned in the insert cavity 98 so as to retain the insert 130 in place in the mold 92.

The insert 130 can include polyoxymethylene (POM), also known as acetal. In one embodiment, the insert 130 can be made of a POM homopolymer such as a POM homopolymer resin sold by E. I. DuPont de Nemours and Company of Wilmington, Del. USA under the trademark Delrin®. In other embodiments, the insert 130 can be made of a POM copolymer. In the illustrated embodiment, the insert 130 consists or consists essentially of POM. In another embodiment, the insert 130 can include a material other than POM so long as a surface of the insert 130 consists or consists essentially of POM where the insert 130 contacts the header body 42.

The header body 42 can be made of epoxy material formed by injecting epoxy resin through the runners 116 and 118 into the mold cavity 96. The epoxy material forms the header body 42 as an epoxy overlayer over components inside the header body 42, such as the core 128. The epoxy material can fill the mold cavity between the housing 20 and the top 100 of the mold cavity 96, as well as adjacent the bottom portion 132 of the insert 130, to form a shape of the header body 42 substantially as illustrated. Once the header body 42 is formed, the pulse generator 12, including the housing 20 and the header 22, can be removed from the mold 92. The insert 130 can then be removed from the header body 42. In embodiments with the pin assembly 122, the pin assembly 122 can also be removed.

Figure 7:
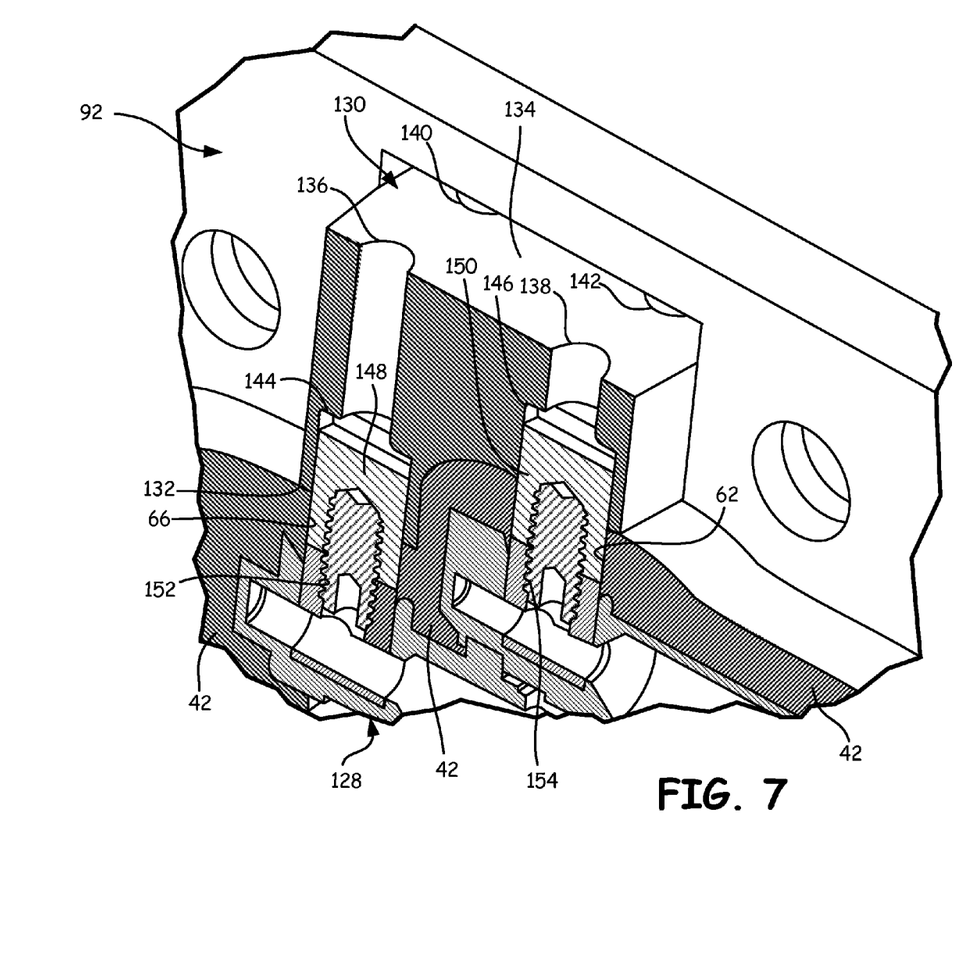
FIG. 7 is a perspective sectional view of the insert positioned in the mold.

FIG. 7 is a perspective sectional view of the insert 130 positioned in the mold 92. The insert 130 defines a plurality of holes 136, 138, 140, and 142 extending from the top portion 134 to the bottom portion 132 of the insert 130. The holes 136, 138, 140, and 142 have a larger diameter near the bottom portion 132 than near the top portion 134, thus forming pin receptacles such as receptacles 144 and 146 of the holes 136 and 138, respectively. Core pins 148 and 150 are positioned partially in the receptacles 144 and 146, respectively. The core pins 148 and 150 are molding pins that extend from the insert 130 to the core 128. The core pins 144 and 146 are also positioned partially in holes 152 and 154 of the core 128.

When material flows into the mold cavity 96 to form the header body 42, the material flows between the core 128 and the insert 130, and flows around the core pins 144 and 146 to form the holes 66 and 62, respectively, in the header body 42. The core pins 144 and 146 can prevent or limit flow of material into the holes 152 and 154, while allowing flow of material over an outer surface of the core 128. The hole 66 in the header body 42 is aligned with the hole 152 in the core 128. The hole 62 in the header body 42 is aligned with the hole 154 in the core 128.

Once the header body 42 is formed and removed from the core 128, the core pins 144 and 146 can be removed from the header body 42 along with the insert 130. Set screws (not shown) can be threaded into the holes 152 and 154 of the core 128. The seal plugs 74 and 70 (shown in FIG. 2) can then be pushed into the holes 66 and 62, respectively, to cover and isolate the set screws from bodily fluids. In some embodiments, the seal plugs 74 and 70 can be pushed at least partially into the holes 152 and 154, respectively.

The core pins 144 and 146 can include polyoxymethylene (POM). In one embodiment, the core pins 144 and 146 can be made of a POM homopolymer such as a POM homopolymer resin sold by E. I. DuPont de Nemours and Company of Wilmington, Del. USA under the trademark Delrin®. In other embodiments, the core pins 144 and 146 can be made of a POM copolymer. In the illustrated embodiment, the core pins 144 and 146 consist or consist essentially of POM. POM can repel epoxy resin, allowing the core pins 144 and 146 to be removed after molding.

In alternative embodiments, the insert 130 can be configured without the holes 136, 138, 140, and 142 as illustrated, so long as the core pins 144 and 146 are positioned in the mold cavity adjacent the insert 130 prior to injecting material into the mold 92. In further alternative embodiments, the core pins 144 and 146 can be omitted, such as in embodiments where the seal plugs 70 and 74 are molded in place.

In such embodiments, the bottom portion 132 of the insert 130 can positioned to contact tops of the seal plugs 70 and 74.

Figure 8:
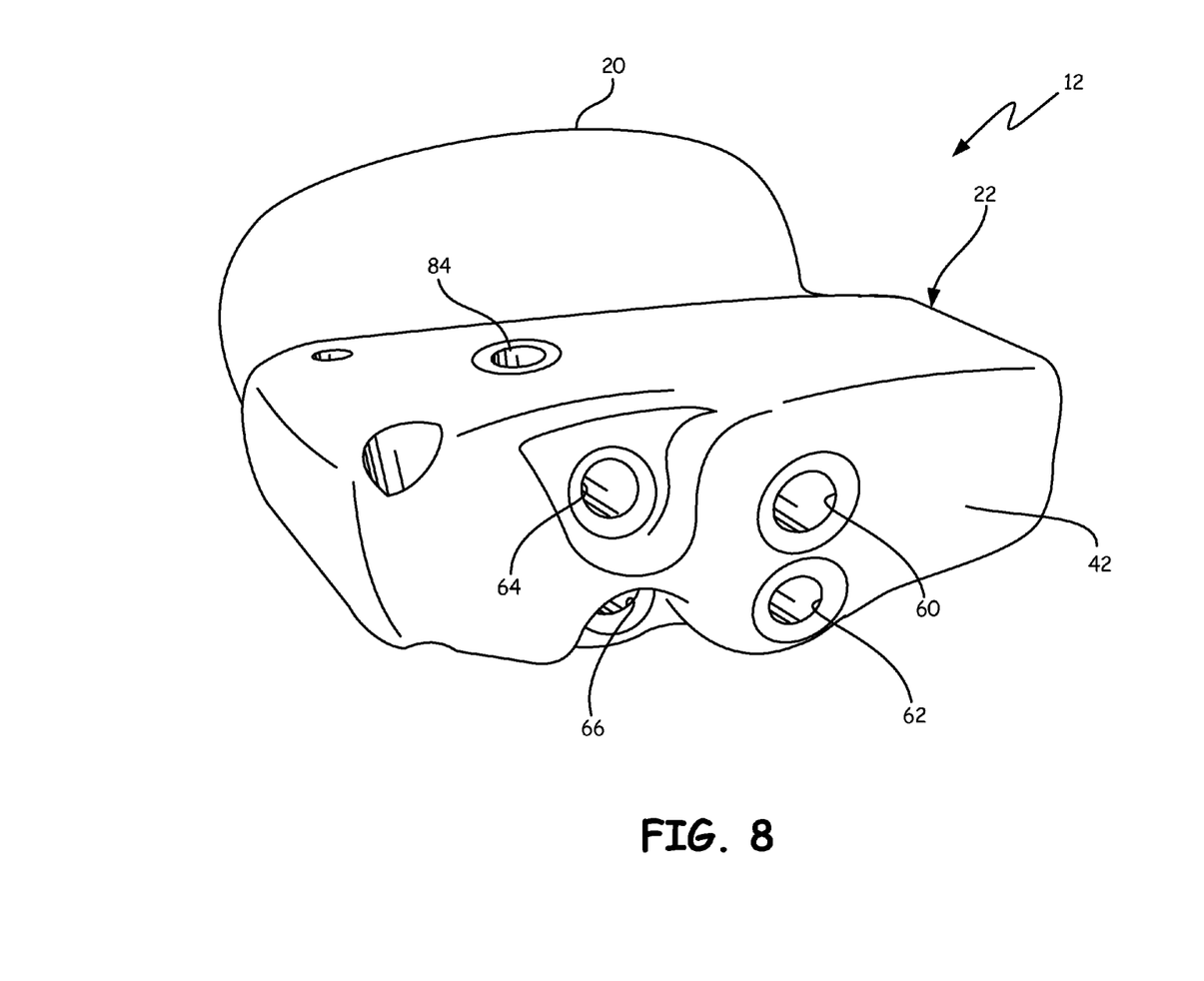
FIG. 8 is a perspective view of the pulse generator with the header molded, prior to insertion of seal plugs.

FIG. 8 is a perspective view of the pulse generator 12 with the header body 42 molded. As shown in FIG. 8, the header body 42 is formed and removed from the mold 92 (shown in FIGS. 3-7), and the insert 130 (shown in FIGS. 6 and 7) as well as the core pins 144 and 146 (shown in FIG. 7) are removed from the header body 42. The holes 60, 62, 64, 66, and 84 are formed, but the plugs 68, 70, 72, 74, and 86 are not yet inserted. The plugs 68, 70, 72, 74, and 86 can then be pushed into the holes 60, 62, 64, 66, and 84 to form the pulse generator 12 as illustrated in FIG. 2.

Thus, the header 22 can be formed using the methods described above. Use of the mold 92, the insert 130, and the core pins 148 and 150 can allow the header body 42 to be formed with the holes 60, 62, 64, and 66 extending through the top surface 50 as well as to form the ridge 82 between the holes 64 and 66. By forming the mold 92 of silicone, the insert 130 of POM, and the core pins 148 and 150 of POM, the epoxy material of the header body 42 can be formed in a shape with relatively tight tolerances, even at relatively thin features such as the ridge 82, and allow for the header body 42 to be released at the end of the mold process. Therefore, seal plugs can be mounted in set screw holes on a top of a device header using a method that is relatively cost effective and reliable.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method comprising:
   providing a mold defining a mold cavity for receiving material to be molded into a molded part, wherein the mold comprises silicone;
   positioning an insert at least partially in the mold such that a portion of the insert defines a portion of the mold cavity, wherein the insert comprises polyoxymethylene;
   positioning a pin in the mold cavity such that the pin extends from the insert and into the mold cavity, wherein the pin defines a shape of a hole of the molded part;
   injecting the material into the mold cavity to substantially fill the mold cavity to form the molded part;
   removing the molded part from the mold; and
   removing the insert and the pin from the molded part.

2. The method of claim 1, wherein the insert is entirely contained in the mold and defines a shape of a portion of an outer surface of the molded part.

3. The method of claim 1, wherein the insert consists or consists essentially of polyoxymethylene homopolymer.

4. The method of claim 1, wherein the material comprises epoxy.

5. The method of claim 1,
   wherein the pin comprises polyoxymethylene.

6. The method of claim 1, wherein the molded part comprises a header for an implantable medical device.

7. The method of claim 1, wherein the insert defines a shape of a ridge on a surface of the molded part extending between holes defined by the molded part.

8. The method of claim 7, wherein the ridge has a thickness of about 0.9 millimeters or less.

9. A method comprising:
providing a mold defining an internal cavity, the internal cavity including a mold cavity for receiving material to be molded into a header for an implantable medical device and including an insert cavity adjacent the mold cavity;
positioning an insert in the internal cavity so that the insert is entirely contained in the mold, wherein at least a portion of the insert is positioned in the insert cavity, and wherein a surface of the insert defines a portion of a top of the mold cavity for forming a portion of a top surface of the header opposite a bottom surface of the header, wherein the bottom surface is configured to be adjacent to a device housing;
injecting the material into the mold cavity to substantially fill the mold cavity to form the header;
removing the header from the mold; and
removing the insert from the header.

10. The method of claim 9, wherein the insert comprises a polyoxymethylene homopolymer.

11. The method of claim 9, wherein the mold comprises silicone.

12. The method of claim 9, wherein the material comprises epoxy.

13. The method of claim 9, and further comprising:
positioning a pin in the mold cavity adjacent the insert prior to injecting the material into the mold cavity, wherein the pin defines a shape of a set screw hole of the header; and
removing the pin from the header after the molded part is formed.

14. The method of claim 13, and further comprising:
inserting a seal plug into the set screw hole, wherein the seal plug has a deformable slit extending through a top of the seal plug through which a tool can be inserted and that is substantially closed to seal and limit fluid flow through the seal plug when the tool is removed.

15. The method of claim 13, wherein the pin comprises a polyoxymethylene homopolymer.

16. The method of claim 13, and further comprising:
positioning a core in the mold cavity adjacent the insert prior to injecting the material into the mold cavity, wherein the pin extends from the core to the insert when the material is injected into the mold cavity.

17. The method of claim 9, and further comprising:
positioning the device housing at least partially in the mold; and
molding the header so as to attach the header to the device housing during molding.

18. The method of claim 9, wherein the insert defines a shape of a portion of an outer surface of the header at a top of the header.

19. A method comprising:
providing a mold defining an internal cavity, the internal cavity including a mold cavity for receiving material to be molded into a header for an implantable medical device and an insert cavity adjacent the mold cavity, wherein the mold comprises silicone;
positioning an insert in the internal cavity so that the insert is entirely contained in the mold, wherein at least a portion of the insert is positioned in the insert cavity, wherein a surface of the insert defines a portion of a top of the mold cavity, and wherein the insert comprises polyoxymethylene;
positioning a pin in the mold cavity adjacent the insert prior to injecting the material into the mold cavity, wherein the pin defines a shape of a set screw hole of the header;
injecting the material into the mold cavity to substantially fill the mold cavity to form the header;
removing the header from the mold; and
removing the insert from the header.

20. The method of claim 19, further comprising:
inserting a seal plug into the set screw hole, wherein the seal plug has a deformable slit extending through a top of the seal plug through which a tool can be inserted and that is substantially closed to seal and limit fluid flow through the seal plug when the tool is removed.

* * * * *